United States Patent [19]

Yamaguchi

[11] 4,436,640
[45] Mar. 13, 1984

[54] GLYCOLATE DITHIOPHOSPHORIC ACIDS, METAL SALTS THEREOF AND OIL COMPOSITIONS CONTAINING THE SALTS

[75] Inventor: Elaine S. Yamaguchi, El Cerrito, Calif.

[73] Assignee: Chevron Research Company, San Francisco, Calif.

[21] Appl. No.: 382,459

[22] Filed: May 27, 1982

[51] Int. Cl.$^3$ .............................................. C10M 1/48
[52] U.S. Cl. ............................ 252/32.7 E; 260/429.9; 260/942; 260/987
[58] Field of Search ................... 260/429.9, 987, 942; 252/32.7 E

[56] References Cited

U.S. PATENT DOCUMENTS 2,895,973  7/1959  Ready ................................. 260/942
3,740,364  6/1973  Schuler et al. ...................... 260/942

Primary Examiner—Jacqueline V. Howard
Attorney, Agent, or Firm—D. A. Newell; J. M. Whitney; V. J. Cavalieri

[57] ABSTRACT

Novel glycolate diesters of dithiophosphoric acid and salts of such esters suitable as additives in oil compositions are disclosed. Oil compositions containing the salts of such esters show improved extreme pressure/antiwear and antioxidant properties.

10 Claims, No Drawings

GLYCOLATE DITHIOPHOSPHORIC ACIDS, METAL SALTS THEREOF AND OIL COMPOSITIONS CONTAINING THE SALTS

BACKGROUND OF THE INVENTION

1. Field of the Invention

The invention relates to novel glycolate diesters of dithiophosphoric acids, their salts, and to oil compositions containing such salts.

2. Description of the Prior Art

It is known to add compounds to oils in order to improve the load-bearing properties, e.g., extreme pressure and/or anti-wear properties thereof.

One class of such compounds are the metal salts of dihydrocarbyl dithiophosphoric acids, e.g., the zinc salts thereof, which are well known as load-bearing additives for lubricating oils. Such salts may be represented by the formula:

$$\left[ \begin{array}{c} RO \\ \diagdown \\ \diagup \\ RO \end{array} \!\!\! \begin{array}{c} S \\ \| \\ P-S \end{array} \right]_n \!\!\!\!\! M$$

wherein:
R is the same or different optionally substituted hydrocarbyl group;
M is a metal; and
n corresponds to the valence of the metal M.

Many types of additives have been proposed, e.g., those in which the optionally substituted hydrocarbyl groups represented by R are the same or different alkyl, cycloalkyl, aryl groups, e.g., see U.S. Pat. Nos. 2,410,642, 2,540,084; and 4,212,751, U.K. Pat. Nos. 723,133 and 852,365, as well as groups derived from alkoxylated alcohols and monoester alcohols, e.g., see U.K. Pat. No. 2,070,054 and U.S. Pat. Nos. 3,102,096 and 4,288,335.

Oil compositions containing the metal glycolate diesters of dithiophosphoric acid of this invention show improved extreme pressure and anti-wear properties as evidenced by valve train wear performance as compared to oil compositions containing the prior art metal dialkyl esters of dithiophosphoric acid.

SUMMARY OF THE INVENTION

A novel class of dithiophosphoric acid diesters and salts thereof have been discovered which are derived from glycolic acid esters.

The invention is particularly concerned with compounds of the general formula:

$$\begin{array}{c} O \\ \| \\ R_1OCCH_2O \\ \diagdown \\ O \quad\quad P-SH \\ \| \quad\quad \diagup \\ R_2OCCH_2O \end{array} \quad\quad I$$

wherein $R_1$ and $R_2$ are the same or different alkyl groups containing 1 to 12 carbon atoms or an alkali or alkaline earth metal or transition metal salt thereof.

The invention further provides oil compositions comprising a major amount of an oil and a minor amount sufficient to inhibit oxidation and wear of a metal salt of the dithiophosphoric acid diesters according to this invention.

DETAILED DESCRIPTION

The novel glycolic diesters of dithiophosphoric acid which comprise compounds of the formula I $$\begin{array}{c} O \\ \| \\ R_1OCCH_2O \\ \diagdown \\ O \quad\quad P-SH \\ \| \quad\quad \diagup \\ R_2OCCH_2O \end{array} \quad\quad I$$

wherein $R_1$ and $R_2$ are defined above, can be prepared by the action of phosphorus pentasulfide on a glycolic acid ester of the Formula II $$\begin{array}{c} O \\ \| \\ ROCCH_2OH \end{array} \quad\quad II$$

wherein R is equivalent to $R_1$ and $R_2$ defined above, with an amount of $P_2S_5$ corresponding to the stoichiometric quantity of $P_2S_5$. This operation may be carried out at a temperature of between about 50° C. and 200° C. and preferably between 70° C. and 150° C.

The glycolic esters of the formula II can be prepared by standard procedures which includes the reaction of an alcohol ROH in which R has the meaning indicated above with glycolic acid in the presence of a sulfuric acid catalyst and optionally in the presence of a solvent. The water of reaction may be removed by distillation or reflux over molecular sieves. After neutralization of the acid catalyst, the glycolate may be isolated and purified by distillation. The molar ratio of glycolic acid to alcohol is in the range of from about 1:1 and 1:15 and preferably between about 1:2 and 1:10. The reaction may be carried out at a temperature of between about 50° C. and 250° C. and preferably between 60° C. and 180° C.

Among the alcohols ROH which may be employed and from which $R_1$ and $R_2$ are derived, are methanol, ethanol, n-butanol, i-butanol, t-butanol, pentanol, propanol, isopropanol, hexanol, octanol, isooctanol, decanol, dodecanol and the like.

The novel salts may be prepared by the neutralization of the diesters of dithiophosphoric acid of the formula I with a basic metal compound such as an alkali or alkaline earth metal or transition metal hydroxide, carbonate or oxide and preferably the metal is selected from the groups IIB, IIIB, IVB, VIB or VII of the Periodic System of Elements and, in particular, zinc.

The reaction may be carried out at a temperature of between about 25° C. and 180° C. with an amount of basic metal compound between the amount stoichiometrically necessary to neutralize the dithiophosphoric acid and twice said stoichiometric amount, and preferably between 1.1 and 1.5 times the stoichiometric amount.

The metal salt so formed may be converted to a different metal salt by double decomposition thereof with a metal salt such as a chloride or sulphate. For example, the sodium salt formed in neutralization may be converted to the zinc salt by reaction thereof with zinc sulphate. The reaction is preferably carried out in the presence of a solvent, e.g., benzene or toluene and under nitrogen. The salt may be isolated from the reaction product mixture by conventional techniques such as by extraction.

The general methods for preparing the dithiophosphoric acid esters and their corresponding metal salts are described in U.S. Pat. Nos. 3,089,850, 3,102,096, 3,293,181 and 3,489,682.

Examples of metal compounds which may be reacted with the dithiophosphoric acid include lithium oxide, lithium hydroxide, lithium carbonate, lithium pentylate, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, molybdenum oxide, and molybdenum oxysulfide.

The salts may be added to any oil, e.g., gasoline, middle distillate fuels, industrial oils, greases, etc. but are particularly suitable as additives to oils of lubricating viscosity, especially those for use in internal combustion engines.

Preferably, the oil basestock is a lubricating oil, fractions of a mineral oil such as petroleum, either naphthenic, paraffinic or as mixed naphthenic/paraffinic base, unrefined, acid-refined, hydrotreated or solvent refined as required for the particular lubricating need. In addition, synthetic oils such as ester lubricating oils and polyalphaolefins, as well as mixtures thereof with mineral oil meeting the viscosity requirements for a particular application either with or without viscosity index improvers may also be used as basestock provided the above compound is soluble therein. The lubricating oil basestock preferably will have a viscosity in the range from about 5 to about 220 centistokes at 100° F. Suitable mineral oils include low, medium, high and very high viscosity index lubricating oils.

The amount of additive present in the composition may vary between wide limits but is suitably from 0.01 to 10% by weight with amounts of from 0.1 to 2% by weight being usual, based on the weight of the composition.

The lubricating compositions according to the invention may contain other components. Examples of such components include viscosity-index improvers including conjugated diolefin block copolymers and low molecular weight methacrylate polymers, dispersants (of the ash and/or ashless type), pour point depressants such as acrylate and methacrylate polymers, anti-oxidants, metal passivators and anti-corrosion agents. If desired, in addition to the present load-bearing additives, the lubricating composition may include other compounds having a load-bearing action.

Additive concentrates are also included within the scope of this invention. They usually include from about 90 to 10 weight percent of an oil of lubricating viscosity and are normally formulated to have about 10 times the additive concentration that would be used in the finished lubricating oil composition. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions.

The following examples are provided to illustrate the invention. It is understood that they are provided for the sake of illustration only and not as a limitation on the scope of the invention.

EXAMPLE 1

Preparation of—n-propyl glycolate

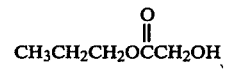

To a 2-liter, three-neck flask equipped with mechanical stirrer, thermometer, Soxhlet extractor, and reflux condenser were added 228 g glycolic acid (3.0 moles) and 720 g n-propanol (12.0 moles). The reaction was stirred until the solid dissolved, and 12 ml concentrated sulfuric acid was added. A thimble full of 3A molecular sieves was placed in the Soxhlet extractor, and the heating mantle was turned on. The reaction was refluxed for 14 hours at approximately 100° C. and the molecular sieves were changed. The reaction was refluxed for an additional seven hours. At this time an IR spectrum of the solution showed carbonyl (C=O) stretch only at 1740 cm$^{-1}$ (ester) and none at 1710 cm$^{-1}$ (acid). The reaction was then neutralized with 150 g NaHCO$_3$, filtered over Super-Cel (SCC), and distilled (50°–52° C. at 1.5 mm) to afford 271 g of n-propyl glycolate (77% yield).

In a similar manner, by substituting an equivalent amount of each of ethanol, isopropanol, n-butanol, sec-butanol and 2-ethylhexanol for n-propanol in the above procedure, the corresponding glycolates were prepared, namely,

| Ester | % Yield |
| --- | --- |
| Methylglycolate | 99 |
| Ethylglycolate | 69 |
| Isopropylglycolate | 55 |
| n-butylglycolate | 59 |
| Sec-butylglycolate | 62 |
| 2-Ethylhexylglycolate | 32 |

EXAMPLE 2

Preparation of t-butylglycolate (A) Silylation of methylglycolate

To a 500-ml flask equipped with reflux condenser, mechanical stirrer, and nitrogen inlet was added 82 g (0.91 mole) methyl glycolate and 73.5 g (0.46 mole) hexamethyldisilazane. The two-phase mixture was stirred at reflux temperature until the lower layer (methyl glycolate) was gone. A pH paper was placed in front of the condenser outlet to check for ammonia (NH$_3$). No evidence of NH$_3$ was found at the end of the reaction. Some solid was left at the bottom of the flask. The liquid was decanted off and distilled under reduced pressure to give 70.5 g (43%), bp 62° C. at approximately 20 mm Hg.

(B) t-Butylglycolate

To a 1-liter, three-neck flask equipped with mechanical stirrer, reflux condenser, nitrogen inlet, and bromine water bubbler was added 98 g Linde 3A-type molecular sieves, 400 ml toluene (dry), 50.0 g methyl glycolate silylate (0.31 mole), 91.4 t-butanol (1.2 moles), and 23.06 g potassium t-butoxide (0.21 mole). The reaction was refluxed overnight. The bromine water was discolored by the offgas, which means that some isobutene was produced by dehydration of t-butanol. The reaction was allowed to cool. The solution was filtered to remove the molecular sieves. The toluene was stripped off, and the solution was distilled (bp 42°–45° C. at 2.7 mm Hg). A mixture of products (3 g) was collected. The composition was determined to contain about 1 g of t-butyl glycolate.

EXAMPLE 3

A. Preparation of O,O'-di(n-propyl glycolate)dithiophosphoric acid

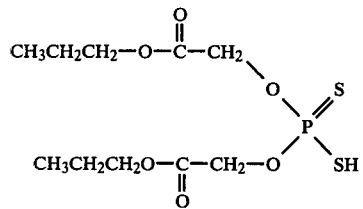

To a dry, nitrogen-flushed three-neck flask equipped with mechanical stirrer, dropping funnel, and a caustic scrubber were added 127.10 g P$_2$S$_5$ (0.57 mole) and 1200 ml toluene. Two hundred and seventy grams of n-propyl glycolate (2.29 moles) was added dropwise over 30 minutes, not allowing the temperature to rise above 30° C. The dropping funnel was then replaced with a condenser, and the reaction mixture was refluxed for one hour. The reaction was allowed to cool to room temperature, and then it was filtered through SCC. The product was not isolated because it was reacted in situ in the next reaction.

B. Preparation of zinc salt of O,O'di-(n-propyl glycolate)dithiophosphoric acid

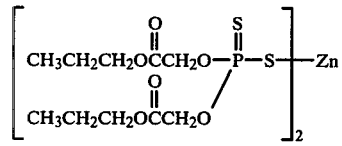

To a nitrogen-flushed flask equiped with mechanical stirrer were added the toluene solution of n-propyl glycolate dithiophosphoric acid (theoretical 377.60 g, 1.14 moles). Zinc oxide (69.80 g, 0.86 mole, 50% excess) was added slowly, and the temperature rose from 25° C. to 45° C. PHydrion paper indicated a pH of approximately 6, which meant the dithiophosphoric acid was neutralized. The solution was stirred at room temperature for 24 hours and then filtered through SCC. The toluene was stripped off on a rotary evaporator, but infrared analysis indicated the presence of water. The zinc salt was redissolved in toluene and MgSO$_4$ (drying agent) was added. The solution was allowed to sit over drying agent for four hours and then was filtered off. The toluene was stripped off to afford 262.2 g (63% yield) of the zinc salt of O,O'-(n-propyl glycolate) dithiophosphoric acid.

In a similar manner, by substituting an equivalent amount of each of the alkylglycolates prepared in Example 1 for the n-propylglycolate in the above procedures, the following alkylglycolate dithiophosphoric acids and corresponding zinc salts were prepared.

| Acids | Zinc Salts |
| --- | --- |
| O,O'—di(Ethylglycolate)dithiophosphoric acid | Ethylglycolate zinc dithiophosphate |
| O,O'—di(Isopropylglycolate) dithio-phosphoric acid | Isopropylglycolate zinc dithiophosphate |
| O,O'—di(n-butylglycolate) dithio-phosphoric acid | n-butylglycolate zinc dithiophosphate |
| O,O'—di(sec-butylglycolate) dithio-phosphoric acid | sec-butylglycolate zinc dithiophosphate |
| O,O'—di(2-ethylhexylglycolate) dithiophosphoric acid | 2-ethylhexylglycolate zinc dithiophosphate |

In a similar manner by substituting an equivalent amount of methylglycolate and t-butylglycolate of Examples 1 and 2 respectively, for the n-propylglycolate in the above procedures, the O,O'-di(methylglycolate) dithiophosphoric acid and O,O'-di(t-butylglycolate) dithiophosphoric acid and their corresponding zinc salts are prepared.

EXAMPLE 4

Formulated oils containing the additives shown in Table 1 were prepared and tested in a Sequence V-D Test method Phase 9-L (according to candidate test for ASTM). This procedure utilizes a Ford 2.3-liter four-cylinder engine. The test method simulates a type of severe field test service characterized by a combination of low speed, low temperature "stop and go" city driving and moderate turnpike operation. The effectiveness of the additives in the oil is measured in terms of the protection provided against valve train wear.

The comparisons were made in a formulated base oil Cit-Con 100N/Cit-Con 200N at 55%/45% containing 30 mmoles/kg of calcium sulfonate, 20 mmoles/kg of a calcium phenate 8.5% of a polymethacrylate V.I. improver, and 3.5% of a 50% concentrate of polyisobutenyl succinimide. Sufficient zinc dithiophosphates were added to give 0.05% (8.1 mmoles/kg) phosphorus to the oil.

TABLE 1

| | | Sequence V-D Test | | | |
| --- | --- | --- | --- | --- | --- |
| | | Cam Lobe Wear, mils | | Follower Weight Loss, mg. | |
| | | SF Spec. Max. | SF Spec. Avg. | | |
| Entry | Additive (8.1 mm/kg) | (2.5) | (1.0) | Max. | Avg. |
| 1. | Zinc di(sec-butyl/mixed 4-methyl-2-pentyl)dithiophosphate | 16.4 | 5.4 | 373 | 195 |
| 2. | Zinc di(isopropyl glycolate) dithiophosphate | 0.8 | 0.6 | +2 | +3 |

EXAMPLE 5

The anti-wear properties for lubricating oil compositions containing the additives prepared according to this invention were tested.

Anti-wear properties are measured by the 4-ball wear and the 4-ball weld tests. The 4-ball wear test is described in ASTM D-2266 and is run at 54° C. for 1 hour at 1800 rpm using steel balls and a 20 and 30 kg load; and the 4-ball weld test is a variation of ASTM D-2783 run at ambient temperature at 1730 rpm until weld point with weights decreased by 5 kg until the pass load is determined.

The results of the 4-ball wear and the 4-ball weld are described in Table 2. The formulation tested contained, in a neutral lubricating oil, 3.5% of a 50% concentrate of polyisobutenyl succinimide 20 mmoles/kg sulfurized calcium phenate, 30 mmoles/kg overbased magnesium sulfonate, 5.5% viscosity index improver, and 18 mmoles/kg product of this invention.

TABLE 2

| | 4-Ball Wear Wear Scar. Diameter mm$^2$ | | 4-Ball Weld | |
|---|---|---|---|---|
| | 20 Kg load | 30 Kg load | Pass Load Kg | Fail Load Kg |
| Zinc di(isopropyl glycolate) dithiophosphate | 0.36 | 0.42 | 195 | 200 |
| Zinc di(ethyl glycolate) dithiophosphate | 0.30 | 0.37 | 195 | 200 |
| Zinc di(n-butyl glycolate) dithiophosphate | 0.35 | 0.41 | 195 | 200 |

What is claimed is:

1. A compound of the formula:

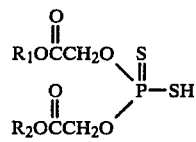

wherein $R_1$ and $R_2$ are the same or different alkyl groups containing 1 to 12 carbon atoms or an alkali or alkaline earth metal or transition metal salt thereof.

2. The compound of claim 1 wherein the salt is a zinc salt.

3. The compound of claim 1 or 2 wherein $R_1$ and $R_2$ is alkyl of 1 to 8 carbon atoms.

4. The compound of claim 1 or 2 wherein $R_1$ and $R_2$ are ethyl, isopropyl, tert-butyl.

5. The compound of claim 1 or 2 wherein $R_1$ or $R_2$ are isopropyl.

6. An oil composition comprising a major proportion of an oil of lubricating viscosity and from 0.01 to 10% by weight based on the composition of a salt as in claim 1 or 2.

7. The oil composition of claim 6 wherein the salt is a zinc salt of O,O'-di(isopropyl glycolate) dithiophosphoric acid.

8. The oil composition of claim 6 wherein the salt is a zinc salt of O,O'-di(ethyl glycolate) dithiophosphoric acid.

9. The oil composition of claim 6 wherein the salt is zinc salt of O,O'-di(tert-butyl glycolate) dithiophosphoric acid.

10. An oil concentrate comprising 10 to 90 weight percent of an oil of lubricating viscosity and from 90 to 10 weight percent of a salt as in claim 1 or 2.

* * * * *